United States Patent
Glue et al.

(10) Patent No.: US 7,776,851 B2
(45) Date of Patent: Aug. 17, 2010

(54) USE OF NEUROKININ ANTAGONISTS IN THE TREATMENT OF URINARY INCONTINENCE

(75) Inventors: Paul William Glue, Flemington, NJ (US); Kevin Hall McAllister, Buschwiller (FR); Eckhard Weber, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/576,052

(22) PCT Filed: Oct. 26, 2004

(86) PCT No.: PCT/EP2004/012081

§ 371 (c)(1), (2), (4) Date: Nov. 1, 2006

(87) PCT Pub. No.: WO2005/039563

PCT Pub. Date: May 6, 2005

(65) Prior Publication Data

US 2007/0149504 A1 Jun. 28, 2007

Related U.S. Application Data

(60) Provisional application No. 60/514,791, filed on Oct. 27, 2003.

(51) Int. Cl.
*A61K 31/55* (2006.01)
(52) U.S. Cl. .................................................. 514/212
(58) Field of Classification Search .................. None
See application file for complete search history.

(56) References Cited

U.S. PATENT DOCUMENTS 5,472,978 A 12/1995 Baker et al.

2002/0115666 A1 8/2002 Dollinger et al.
2004/0058914 A1 * 3/2004 Doi et al. .................... 514/220

FOREIGN PATENT DOCUMENTS

| EP | EP1352659 | | 10/2003 |
|----|-----------|---|---------|
| EP | EP1369129 | | 12/2003 |
| WO | WO98/07694 | | 2/1998 |
| WO | 02/051440 | * | 7/2002 |
| WO | WO03/066062 | | 8/2003 |

OTHER PUBLICATIONS

Butera, "Recent approaches to the treatment of urinary incontinence: a survey of patent activity from 1995 to 1998," Exp. Opin. Ther. Patents, (1998), 8(8): 1017-1035.

Lecci, "Involvement of spinal tachykinin NK1 and NK2 receptors in detrusor hyperreflexia during chemical cystitis in anaesthetized rats" European Journal of Pharmacology 259 (1994) 129-135.

* cited by examiner

*Primary Examiner*—Phyllis G. Spivack
(74) *Attorney, Agent, or Firm*—Montgomery, McCracken, Walker & Rhoads, LLP; Robert R. Axenfeld; David J. Roper

(57) ABSTRACT

This invention relates to compounds of formula I, wherein the $R^1$, $R^2$, $R^3$, $R^4$, $R^5$, $R^6$ and $R^7$ are as defined in the specification, and, in particular, their use as pharmaceuticals, for use in the treatment of urinary incontinence.

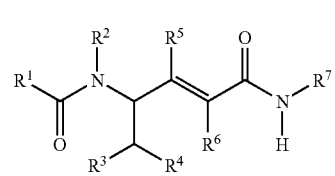

2 Claims, 2 Drawing Sheets

Figure 1: Inhibitory effects of DNK 333 on 5-HTP – stimulated overactive urinary bladder responses in the conscious guinea-pig.
(Mean ± SEM, # $P < 0.05$ vs. control, * $P < 0.05$ vs. 5-HTP, RM ANOVA post-hoc Tukey, n = number of animals)
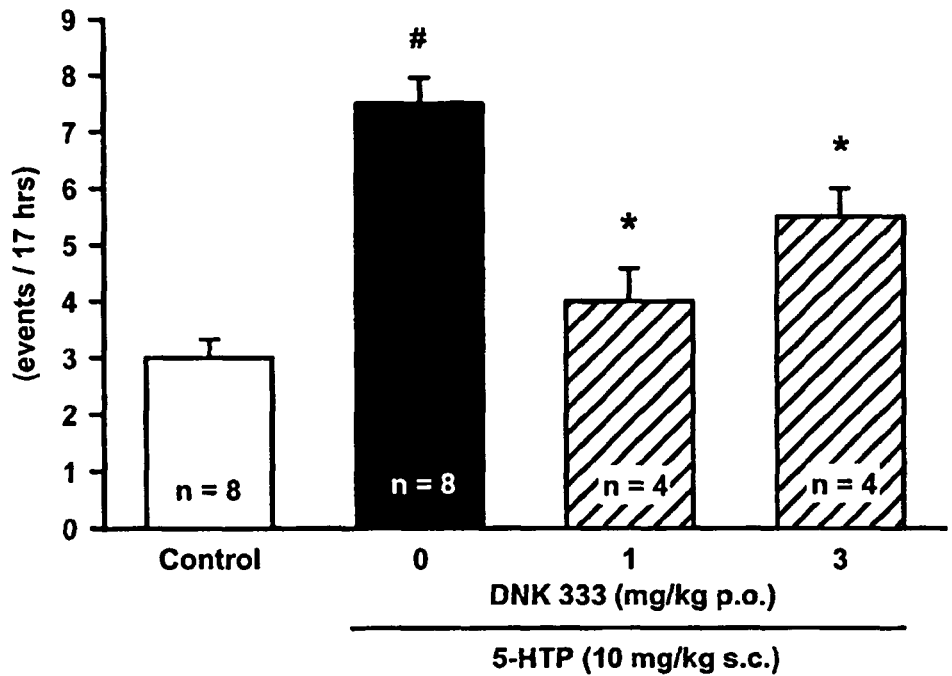
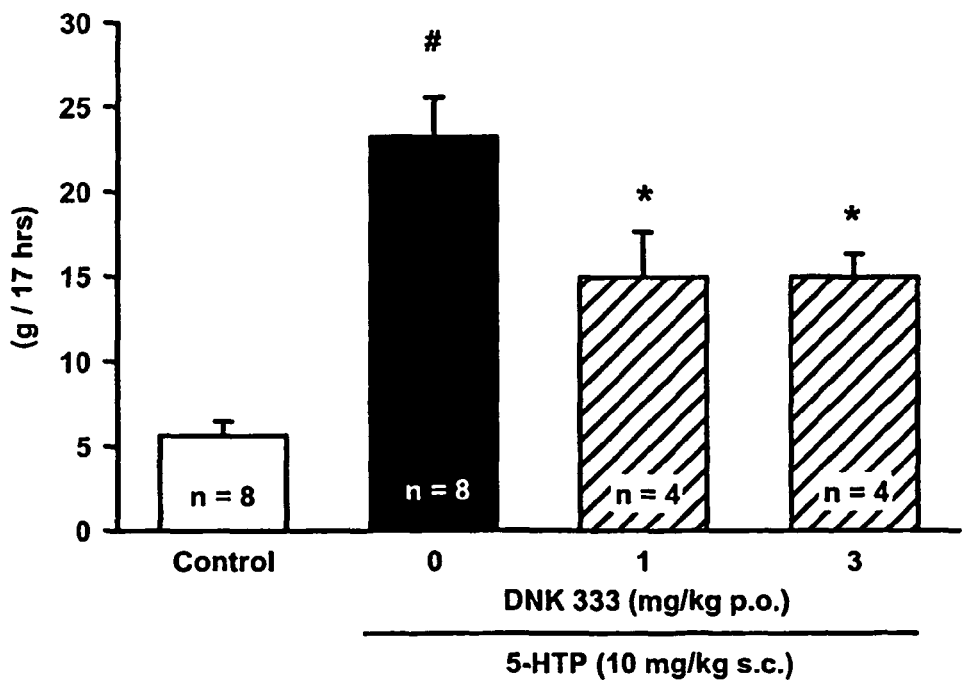

Figure 2: Inhibitory effects of DNK 333 on substance P – stimulated detrusor contractility in longitudinal muscle-nerve preparations from the guinea-pig urinary bladder.
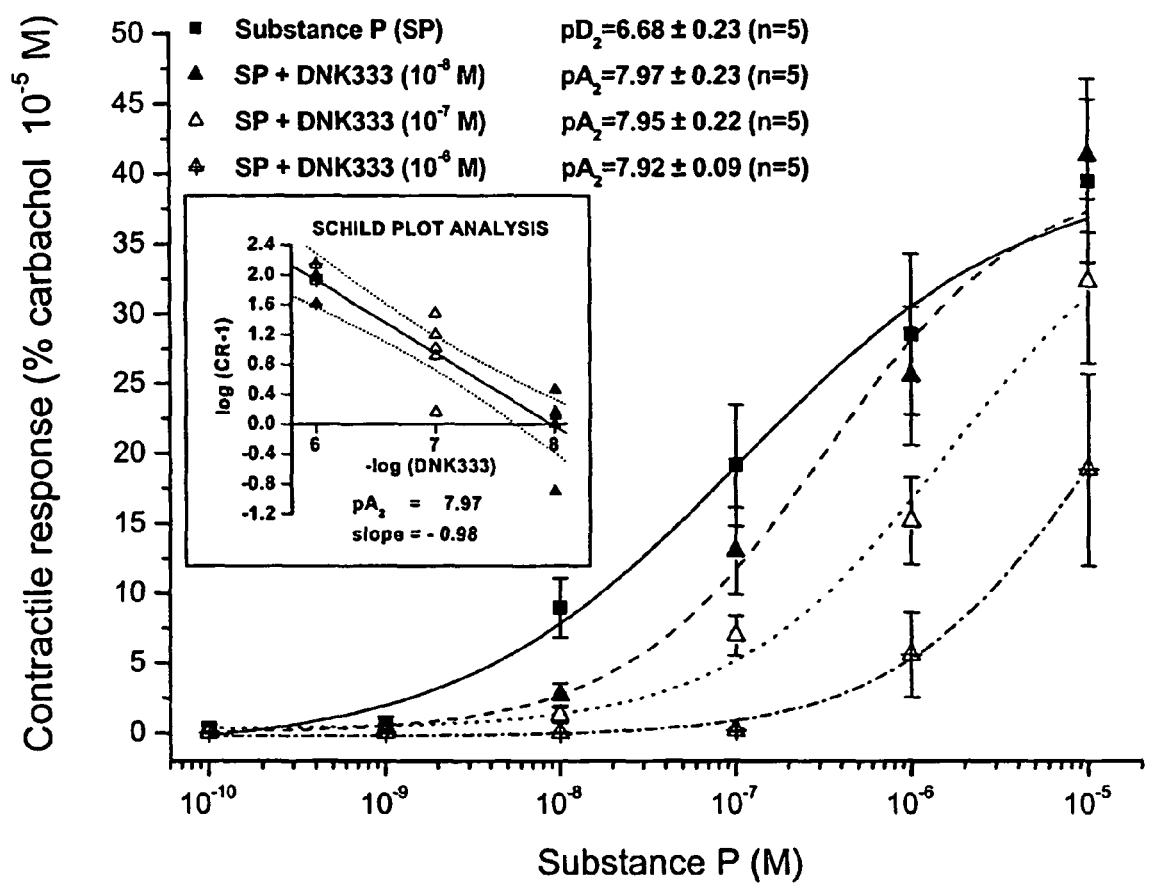
(Mean ± SEM, n = number of preparations)

USE OF NEUROKININ ANTAGONISTS IN THE TREATMENT OF URINARY INCONTINENCE

This application claims benefit of U.S. Provisional Application No. 60/514,791, filed Oct. 27, 2003.

This invention relates to compounds of formula I and, in particular, their use as pharmaceuticals, e.g. use in urinary incontinence.

The invention provides, in one aspect, a method of treating urinary incontinence in a subject in need of such treatment that comprises administering to said subject an effective amount of a compound of formula I

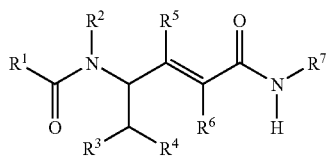

in free form or in the form of a pharmaceutically acceptable salt, wherein $R^1$ is phenyl that is unsubstituted or is substituted by 1, 2 or 3 substituents selected from the group halogen, $C_1$-$C_7$-alkyl, trifluoromethyl, hydroxy and $C_1$-$C_7$-alkoxy, $R^2$ is hydrogen or $C_1$-$C_7$-alkyl, $R^3$ is hydrogen, $C_1$-$C_7$-alkyl or phenyl that is unsubstituted or is substituted by 1, 2 or 3 substituents selected from the group halogen, $C_1$-$C_7$-alkyl, trifluoromethyl, hydroxy and $C_1$-$C_7$-alkoxy, $R^4$ is phenyl that is unsubstituted or is substituted by 1, 2 or 3 substituents selected from the group halogen, $C_1$-$C_7$-alkyl, trifluoromethyl, hydroxy and $C_1$-$C_7$-alkoxy; or is naphthyl, 1H-indol-3-yl or 1-$C_1$-$C_7$-alkyl-indol-3-yl, $R^5$ and $R^6$ are each independently of the other hydrogen or $C_1$-$C_7$-alkyl, at least one of $R^5$ and $R^6$ being hydrogen, and $R^7$ is $C_3$-$C_8$-cycloalkyl, D-azacycloheptan-2-on-3-yl or L-azacycloheptan-2-on-3-yl.

The invention provides, in another aspect, the use of a compound of formula I as hereinbefore defined in free form or in the form of a pharmaceutically acceptable salt for the preparation of a medicament for the treatment of urinary incontinence.

Treatment of urinary incontinence in accordance with the invention includes symptomatic treatment, i.e. treatment of established symptoms, as well as prophylactic (preventative) treatment.

Urinary incontinence to be treated in accordance with the invention may be, for example, urge incontinence, stress incontinence, mixed urge/stress incontinence, or neurogenic incontinence (unstable detrusor and detrusor hyperreflexia, decreased bladder compliance, sensory urgency, bladder-related visceral pain).

Terms used in this specification have the following meanings:

"$C_1$-$C_7$-alkyl" as used herein denotes straight chain or branched alkyl having 1 to 17 carbon atoms, for example, methyl, ethyl, n-propyl, isopropyl, n-butyl, isobutyl, sec-butyl, tert-butyl, n-pentyl, neopentyl, n-hexyl or n-heptyl. Preferably $C_1$-$C_7$-alkyl is $C_1$-$C_4$-alkyl, especially methyl or ethyl, and more especially methyl.

"Halo" or "halogen" as used herein denotes a element belonging to group 17 (formerly group VII) of the Periodic Table of Elements, which may be, for example, fluorine, chlorine, bromine or iodine.

"Halophenyl" as used herein denotes phenyl monosubstituted by halo, for example, (fluoro-, chloro-, bromo- or iodo-) phenyl, preferably fluorophenyl or chlorophenyl, especially 4-fluorophenyl or 4-chlorophenyl, and more especially 4-chlorophenyl.

"Dihalophenyl" as used herein denotes phenyl disubstituted by halo, for example, dichlorophenyl, difluorophenyl or chlorofluorophenyl, preferably dichlorophenyl or difluorophenyl, especially 3,4-dichlorophenyl or 3,4-difluorophenyl, and more especially 3,4-dichlorophenyl.

"Trihalophenyl" as used herein denotes phenyl trisubstituted by halo, for example, trifluorophenyl or trichlorophenyl.

1-$C_1$-$C_7$-alkyl-indol-3-yl is, for example, 1-methyl-indol-3-yl.

$C_3$-$C_8$-Cycloalkyl—and analogously $C_5$-$C_7$-cycloalkyl—is in each case a cycloalkyl radical having the number of ring carbon atoms indicated. $C_3$-$C_8$-Cycloalkyl is therefore, for example, cyclopropyl, cyclobutyl, cyclopentyl, cyclohexyl, cycloheptyl or cyclooctyl, preferably cyclohexyl.

D-Azacycloheptan-2-on-3-yl corresponds to the following group

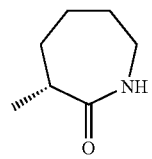

which is derived from D(+)-epsilon-caprolactam (amino-) substituted in the 3-position [≈D-3-amino-epsilon-caprolactam=(R)-3-amino-hexahydro-2-azepinone]. Analogously, L-aza-cycloheptan-2-on-3-yl corresponds to the group

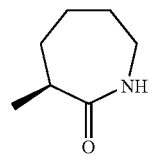

which is derived from L(−)-epsilon-caprolactam (amino-) substituted in the 3-position [≈L-3-amino-epsilon-caprolactam=(S)-3-amino-hexahydro-2-azepinone].

The compounds of formula I may be of formula IA

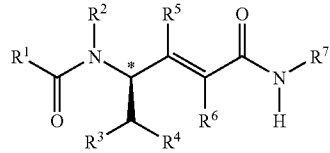

where * denotes the R configuration, or of formula IB

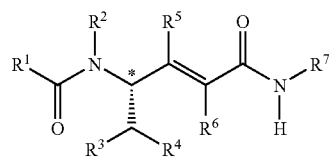

where * denotes the S configuration, where $R^1$, $R^2$, $R^3$, $R^4$, $R^5$, $R^6$ and $R^7$ are as hereinbefore defined.

Compounds of formula IA are usually preferred for use in accordance with the invention.

Compounds of formula I having a basic group may, for example, form acid addition salts with suitable mineral acids, such as hydrohalic acids, sulfuric acid or phosphoric acid, for example hydrochlorides, hydrobromides, sulfates, hydrogen sulfates or phosphates. Where the compounds of formula I contain an acid group, corresponding salts with bases are also possible, for example corresponding alkali metal or alkaline earth metal salts, for example sodium, potassium or magnesium salts, or salts with ammonia or organic amines, for example ammonium salts.

The invention relates preferably to the use of compounds of formula I wherein $R^1$ is phenyl, 3,5-bistrifluoromethyl-phenyl or 3,4,5-trimethoxyphenyl, $R^2$ is hydrogen or $C_1$-$C_7$-alkyl, $R^3$ is hydrogen or phenyl, $R^4$ is phenyl, halo-phenyl, dihalo-phenyl, trihalo-phenyl, 2-naphthyl, 1H-indol-3-yl or 1-$C_1$-$C_7$-alkyl-indol-3-yl, $R^5$ and $R^6$ are each independently of the other hydrogen or $C_1$-$C_7$-alkyl, at least one of $R^5$ and $R^6$ being hydrogen, and $R^7$ is $C_5$-$C_7$cycloalkyl, D-azacycloheptan-2-on-3-yl or L-azacycloheptan-2-on-3-yl.

The invention relates especially to the use of compounds of formula I wherein $R^1$ is 3,5-bistrifluoromethyl-phenyl, $R^2$ is hydrogen, methyl or ethyl, $R^3$ is hydrogen or phenyl, $R^4$ is phenyl, 4-chlorophenyl, 4-fluorophenyl, 3,4-dichloro-phenyl, 3,4-difluoro-phenyl, 3-fluoro-4-chloro-phenyl, 3,4,5-trifluoro-phenyl, 2-naphthyl, 1H-indol-3-yl or 1-methyl-indol-3-yl, $R^5$ and $R^6$ are each independently of the other hydrogen or methyl, at least one of $R^5$ and $R^6$ being hydrogen, and $R^7$ is cyclohexyl, D-azacycloheptan-2-on-3-yl or L-azacycloheptan-2-on-3-yl.

The invention relates more especially to the use of compounds of formula I wherein $R^1$ is 3,5-bistrifluoromethyl-phenyl, $R^2$ is hydrogen or methyl, $R^3$ is hydrogen or phenyl, $R^4$ is phenyl, 4-chlorophenyl, 3,4-dichloro-phenyl, 2-naphthyl, 1H-indol-3-yl or 1-methyl-indol-3-yl, $R^5$ and $R^6$ are hydrogen, and $R^7$ is cyclohexyl, D-azacycloheptan-2-on-3-yl or L-azacycloheptan-2-on-3-yl.

Special mention should be made of each of the following sub-groups of a group of compounds of formula I:

(1) compounds of formula I wherein $R^7$ is D-azacycloheptan-2-on-3-yl; (2) compounds of formula I wherein $R^5$ and $R^6$ are hydrogen; (3) compounds of formula I wherein $R^1$ is phenyl, 3,5-bistrifluoromethyl-phenyl or 3,4,5-trimethoxyphenyl; and (4) compounds of formula I in free form, that is to say not in the form of a salt.

Specific examples of compounds of formula I include:

(4R)-[N'-methyl-N'-(3,5-bistrifluoromethyl-benzoyl)-amino]-5-(1-methyl-indol-3-yl)-pent-2-enoic acid N-[(R)-epsilon-caprolactam-3-yl]-amide, (4R)-[N'-methyl-N'-(3,5-bistrifluoromethyl-benzoyl)-amino]-5-(1-methyl-indol-3-yl)-pent-2-enoic acid N-[(S)-epsilon-caprolactam-3-yl]-amide, (4R)-[N'-methyl-N'-(3,5-bistrifluoromethyl-benzoyl)-amino]-5-(1-methyl-indol-3-yl)-pent-2-enoic acid N-cyclohexyl-amide, (4R)-[N'-methyl-N'-(3,5-bistrifluoromethyl-benzoyl)-amino]-5-(1-methyl-indol-3-yl)-2-methyl-pent-2-enoic acid N-cyclohexyl-amide, (4R)-[N'-methyl-N'-(3,5-bistrifluoromethyl-benzoyl)-amino]-5-(1-methyl-indol-3-yl)-2-methyl-pent-2-enoic acid N-[(R)-epsilon-caprolactam-3-yl]-amide, (4R)-[N'-methyl-N'-(3,5-bistrifluoromethyl-benzoyl)-amino]-5-(1-methyl-indol-3-yl)-2-methyl-pent-2-enoic acid N-[(S)-epsilon-caprolactam-3-yl]-amide, (4R)-(N'-methyl-N'-benzoyl-amino)-5-(1-methyl-indol-3-yl)-2-methyl-pent-2-enoic acid N-[(R)-epsilon-caprolactam-3-yl]-amide, (4R)-[N'-methyl-N'-(3,5-bistrifluoromethyl-benzoyl)-amino]-5-(naphth-2-yl)-pent-2-enoic acid N-[(R)-epsilon-caprolactam-3-yl]-amide, (4R)-(N'-methyl-N'-benzoyl)-amino-5-(naphth-2-yl)-pent-2-enoic acid N-[(R)-epsilon-caprolactam-3-yl]-amide, (4R)-[N'-methyl-N'-(3,5-bistrifluoromethyl-benzoyl)-amino]-5-(naphth-2-yl)-2-methyl-pent-2-enoic acid N-[(R)-epsilon-caprolactam-3-yl]-amide, (4R)-[N'-methyl-N'-(3,4,5-trimethoxy-benzoyl)-amino]-5-(naphth-2-yl)-2-methyl-pent-2-enoic acid N-[(R)-epsilon-caprolactam-3-yl]-amide, (4R)-[N'-methyl-N'-(3,5-bistrifluoromethyl-benzoyl)-amino]-5-(naphth-2-yl)-2-methyl-pent-2-enoic acid N-[(S)-epsilon-caprolactam-3-yl]-amide, (4R)-[N'-methyl-N'-(3,5-bistrifluoromethyl-benzoyl)-amino]-5-(naphth-2-yl)-2-methyl-pent-2-enoic acid N-cyclohexyl-amide,
(4R)-[N'-methyl-N'-(3,5-bistrifluoromethyl-benzoyl)-amino]-5-(1-methyl-indol-3-yl)-pent-2-enoic acid N-[(S)-epsilon-caprolactam-3-yl]-amide,
(4R)-[N'-methyl-N'-(3,5-bistrifluoromethyl-benzoyl)-amino]-4-(4-chlorobenzyl)-but-2-enoic acid N-[(R)-epsilon-caprolactam-3-yl]-amide,
(4R)-[N'-methyl-N'-(3,5-bistrifluoromethyl-benzoyl)-amino]-4-(4-chlorobenzyl)-but-2-enoic acid N-[(S)-epsilon-caprolactam-3-yl]-amide,
(4R)-[N'-methyl-N'-(3,5-bistrifluoromethyl-benzoyl)-amino]-4-(4-chlorobenzyl)-but-2-enoic acid N-cyclohexyl-amide,
(4R)-[N'-methyl-N'-(3,5-bistrifluoromethyl-benzoyl)-amino]-4-(3,4-dichlorobenzyl)-but-2-enoic acid N-cyclohexyl-amide,
(4R)-[N'-methyl-N'-(3,5-bistrifluoromethyl-benzoyl)-amino]-4-(3,4-difluorobenzyl)-but-2-enoic acid N-cyclohexyl-amide,
(4R)-[N'-methyl-N'-(3,5-bistrifluoromethyl-benzoyl)-amino]-5-(4-chlorophenyl)-2-methyl-pent-2-enoic acid N-cyclohexylamide,
(4R)-[N'-methyl-N'-(3,5-bistrifluoromethyl-benzoyl)-amino]-5-(4-chlorophenyl)-2-methyl-pent-2-enoic acid N-[(R)-epsilon-caprolactam-3-yl]-amide,
(4R)-[N'-methyl-N'-(3,5-bistrifluoromethyl-benzoyl)-amino]-4-(4-chlorobenzyl)-2-methyl-but-2-enoic acid [(S)-epsilon-caprolactam-3-yl]-amide,
(4R)-[N'-ethyl-N'-(3,5-bistrifluoromethyl-benzoyl)-amino]-5-(4-chlorophenyl)-pent-2-enoic acid N-[(S)-epsilon-caprolactam-3-yl]-amide,
(4R)-[N'-methyl-N'-(3,5-bistrifluoromethyl-benzoyl)-amino]-5-(4-chlorophenyl)-3-methyl-pent-2-enoic acid N-cyclohexyl-amide,
(4R)-[N'-methyl-N'-(3,5-bistrifluoromethyl-benzoyl)-amino]-4-(4-chlorobenzyl)-3-methyl-but-2-enoic acid [(R)-epsilon-caprolactam-3-yl]-amide,
(4R)-[N'-methyl-N'-(3,5-bistrifluoromethyl-benzoyl)-amino]-4-(4-chlorobenzyl)-but-2-enoic acid N-[(R)-epsilon-caprolactam-3-yl]-amide,
(4R)-4-[N'-methyl-N'-(3,5-bistrifluoromethyl-benzoyl)-amino]-4-(3,4-dichlorobenzyl)-but-2-enoic acid N-[(R)-epsilon-caprolactam-3-yl]-amide,
(4R)- and (4S)-4-[N'-methyl-N'-(3,5-bistrifluoromethyl-benzoyl)-amino]-4-(3-fluoro-4-chlorobenzyl)-but-2-enoic acid N-[(R)-epsilon-caprolactam-3-yl]-amide,
(4R)- and (4S)-4-[N'-methyl-N'-(3,5-bistrifluoromethyl-benzoyl)-amino]-4-(3,4-difluorobenzyl)-but-2-enoic acid N-[(R)-epsilon-caprolactam-3-yl]-amide,
(4R)- and (4S)-4-[N'-methyl-N'-(3,5-bistrifluoromethyl-benzoyl)-amino]-4-(3,4-dibromobenzyl)-but-2-enoic acid N-[(R)-epsilon-caprolactam-3-yl]-amide,
(4R)- and (4S)-4-[N'-methyl-N'-(3,5-bistrifluoromethyl-benzoyl)-amino]-4-(3,4,5-trifluorobenzyl)-but-2-enoic acid N-[(R)-epsilon-caprolactam-3-yl]-amide,
(4R)- and (4S)-4-[N'-methyl-N'-(3,5-bistrifluoromethyl-benzoyl)-amino]-4-(4-fluorobenzyl)-but-2-enoic acid N-[(R)-epsilon-caprolactam-3-yl]-amide,
(4R)- and (4S)-[N'-(3,5-bistrifluoromethyl-benzoyl)-N'-methyl-amino]-5,5-diphenyl-pent-2-enoic acid N-[(S)-epsilon-caprolactam-3-yl]-amide,
(4S)-4-[N'-methyl-N'-(3,5-bistrifluoromethylbenzoyl)amino]-4-(3,4-dichlorobenzyl)-but-2-enoic acid N-[(R)-epsilon-caprolactam-3-yl]-amide,
(4R)-4-[N'-methyl-N'-(3,5-bistrifluoromethylbenzoyl)amino]-4-(3,4-dichlorobenzyl)-but-2-enoic acid N-[(S)-epsilon-caprolactam-3-yl]-amide, and
(4S)-4-[N'-methyl-N'-(3,5-bistrifluoromethylbenzoyl)amino]-4-(3,4-dichlorobenzyl)-but-2-enoic acid N-[(S)-epsilon-caprolactam-3-yl]-amide.

The invention relates most importantly to the use of (4R)-4-[N'-methyl-N'-(3,5-bistrifluoromethylbenzoyl)amino]-4-(3,4-dichlorobenzyl)-but-2-enoic acid N-[(R)-epsilon-caprolactam-3-yl]-amide, i.e. a compound of formula

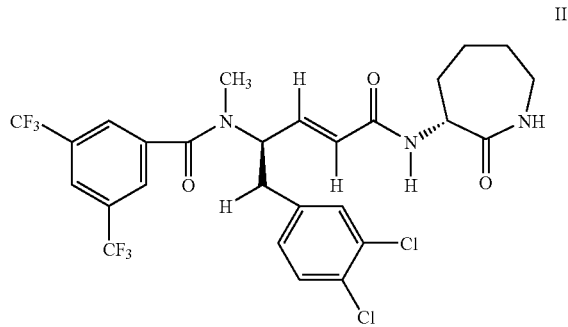

II

The compounds of formula I, in free or pharmaceutically acceptable salt form, may be prepared as described in international patent application WO 98/07694. As mentioned therein, they may be in the form of their hydrates and/or may include other solvents, for example solvents which may have been used for the crystallisation of compounds in solid form.

Depending upon the nature of the variables and the corresponding number of centres of asymmetry and also upon the starting materials and procedures chosen, the compounds of formula I may be obtained in the form of mixtures of stereoisomers, for example mixtures of diastereoisomers or mixtures of enantiomers, such as racemates, or possibly also in the form of pure stereoisomers. Mixtures of diastereoisomers obtainable in accordance with the process or by some other method can be separated in customary manner into mixtures of enantiomers, for example racemates, or into individual diastereoisomers, for example on the basis of the physico-chemical differences between the constituents in known manner by fractional crystallisation, distillation and/or chromatography. Advantageously the more active isomer is isolated.

Mixtures of enantiomers, especially racemates, obtainable in accordance with the process or by some other method can be separated into the individual enantiomers by known methods, for example by recrystallisation from an optically active solvent, with the aid of micro-organisms, by chromatography and/or by reaction with an optically active auxiliary compound, for example a base, acid or alcohol, to form mixtures of diastereoisomeric salts or functional derivatives, such as esters, separation thereof and freeing of the desired enantiomer. Advantageously the more active enantiomer is isolated.

In the treatment of urinary incontinence, compounds of formula I, in free form or in pharmaceutically acceptable salt form, may be administered by any appropriate route, for example orally, e.g. in tablet or capsule form, parenterally, for example in the form of an injectable solution or suspension, intravescically, for example in the form of an infusable solution or suspension, percutaneously, for example in the form of a skin patch, or intranasally, for example in the form of an aerosol or other atomisable formulation using an appropriate intranasal delivery device, e.g. a nasal spray such as those known in the art.

The compound of formula I in free or salt form may be administered in a pharmaceutical composition together with a pharmaceutically acceptable diluent or carrier. Such compositions may be as described in international patent application WO 98/07694, for example tablets, capsules, injection solutions, infusion solutions, or inhalation suspensions as described in Examples A to E of WO 98/07694, or skin patches, or may be prepared using other formulating ingredients and techniques known in the art.

The dosage of the compound of formula I in free or salt form can depend on various factors, such as the activity and duration of action of the active ingredient, the severity of the condition to be treated, the mode of administration, the species, sex, age and weight of the subject and/or its individual condition. In a normal case the daily dose for administration, for example oral administration, to an animal, including human, weighing about 75 kg is estimated to be from approximately 0.1 mg to approximately 1000 mg, especially from approximately 5 mg to approximately 200 mg. That dose may be administered, for example, in a single dose or in several part doses of, for example, from 5 to 100 mg.

In the treatment of urinary incontinence, compounds of formula I or salts thereof may be used as co-therapeutic agents in combination with other drug substances, for example as potentiators of therapeutic activity of the other drugs or as a means of reducing required dosaging or potential side effects of such drugs. The drugs may be together in the same composition or compounds of formula I or salts thereof may be administered in separate form before, simultaneously with or after the other drug substances. The other drugs may be selected from anticholinergics such as oxybutinin, tolterodine, propantheline, darifenacin and dicyclomine; anticholinergics/calcium channel antagonists such as propiverine, alpha-adrenergic antagonists such as prazosin and doxazosin; beta-adrenergic agonists such as clenbuterol, selective beta 3 adrenergic agonists; selective norepinephrine and serotonin reuptake inhibitors such as venlafaxine and duloxetine, selective norepinephrine uptake inhibitors such as reboxetine; selective serotonin reuptake inhibitors such as fluoxetine, paroxetine and sertraline; non-selective monoamine uptake inhibitors such as imipramine, desipramine and amitriptyline; prostaglandin synthesis inhibitors such as flurbiprofen, ibuprofen and COX-2 inhibitors; vasopressin analogues such as desmopressin; potassium channel agonists such as pinacidil and cromkalim; calcium channel antagonists; GABA-B agonists such as baclofen; CGRP antagonists; neurokinin receptor antagonists; P2X antagonists; NO donors such as nitroflurbiprofen; tachykinin agonists such as capsaicin and resiniferatoxin; vanilloid VR1 antagonists; cannabinoid agonists; phosphodiesterase-1 inhibitors such as vinpocetine; and oestrogens such as oestriol.

The effectiveness of a compound of formula I or a combination as hereinbefore described in the treatment of urinary incontinence may be demonstrated by (a) administering the compound to a subject orally in a dose as hereinbefore described, preferably 200 mg per day, for a period of, for example, 2 weeks, (b) carrying out cystometric measurements prior to and during that treatment period, e.g. by measuring bladder fill volume (bladder capacity) at onset of urge according to known methods, for example as described by Bristow S E and Hilton P, *Bailliere's Clin. Obstet. Gynecol.* 2000, 14:227-249, and/or (c) recording the daily frequency of episodes of incontinence, nocturia and the frequency of urination (see Bristow and Hilton, op. cit.), and (d) comparing the results with those obtained following administration of placebo over the same time period.

The utility of a compound of formula I in the treatment of the disorders hereinbefore described may be demonstrated in an in vivo model of stimulated micturition, for example as described hereinafter in Example 1, or in a isolated detrusor contractility model, for example as described hereinafter in Example 2.

FIG. 1: Inhibitory effects of DNK 333 on 5-HP—stimulated overactive urinary bladder responses in the conscious guinea-pig.

FIG. 2: Inhibitory effects of DNK 333 on substance P—stimulated detrusor contractility in longitudinal muscle-nerve preparations from the guinea-pig urinary bladder.

The invention is illustrated by the following Examples.

EXAMPLES

Example 1

In conscious guinea pigs, an experimental paradigm is applied to stimulate micturition through subcutaneous administration of 5-hydroxytryptophan (5-HTP, 10 mg/kg). The measurement of both voiding frequency and micturition volume is used to quantify the effects of the compound of formula II (Belis, et al 1996). Vehicle or the compound of formula II (1 and 3 mg/kg) are dosed orally one hour prior to the stimulation with 5-HTP.

The effects of vehicle and the compound of formula II are assessed over 17 hours in 4 to 8 animals. S-HTP significantly increases the voiding frequency (2.7-fold) and the micturition volume (4.5-fold) as compared to control animals. The compound of formula II attenuates the overactive bladder responses upon stimulation with 5-HTP. At doses of 1 and 3 mg/kg p.o., it decreases the voiding frequency by 45.4%±7.1% and 26.2%±7.1% and the micturition volume by 32.9%±4.5% and 36.6%±6.2%, respectively (mean±SEM).

The effects are statistically significant at both doses tested ($p<0.05$; RM ANOVA, post-hoc Tukey test). See also FIG. 1.

TABLE 1

Primary data on the inhibitory effects of DNK 333 on 5-HTP - stimulated overactive urinary bladder responses in conscious guinea-pigs.

| Voiding frequency (events/17 hrs) | | | | 5-HTP % increase | DNK333 % inhibition |
|---|---|---|---|---|---|
| Animal | Control | 5-HTP (10 mg/kg sc) | 5-HTP + DNK 333 (1 mg/kg po) | | |
| 1F | 3 | 8 | 5 | 267 | 37.5 |
| 2F | 3 | 9 | 3 | 300 | 66.7 |
| 3F | 3 | 8 | 5 | 267 | 37.5 |
| 4F | 3 | 5 | 3 | 167 | 40.0 |
| Mean | 3.0 | 7.5 | 4.0 | 250.0 | 45.4 |
| SEM | 0.0 | 0.9 | 0.6 | 28.9 | 7.1 |
| N | 4 | 4 | 4 | 4 | 4 |
| P RM ANOVA (post-hoc Turkey) | | | 0.041 vs 5-HTP | | |

| Voiding frequency (events/17 hrs) | | | | 5-HTP % increase | DNK333 % inhibition |
|---|---|---|---|---|---|
| Animal | Control | 5-HTP (10 mg/kg sc) | 5-HTP + DNK 333 (3 mg/kg po) | | |
| 1G | 2 | 9 | 6 | 450 | 33.3 |
| 2G | 3 | 7 | 6 | 233 | 14.3 |
| 3G | 2 | 7 | 6 | 350 | 14.3 |
| 4G | 5 | 7 | 4 | 140 | 42.9 |
| Mean | 3.0 | 7.5 | 5.5 | 293.3 | 26.2 |
| SEM | 0.7 | 0.5 | 0.5 | 67.6 | 7.1 |
| N | 4 | 4 | 4 | 4 | 4 |
| P RM ANOVA (post-hoc Turkey) | | | 0.027 vs 5-HTP | | |
| Mean | 3.0 | 7.5 | | 271.7 | |
| SEM | 0.3 | 0.5 | | 35.0 | |
| N | 8 | 8 | | 8 | |
| P RM ANOVA (post-hoc Turkey) | | 0.001 vs Control | | | |

| Micturition volume (g/17 hrs) | | | | 5-HTP % increase | DNK333 % inhibition |
|---|---|---|---|---|---|
| Animal | Control | 5-HTP (10 mg/kg sc) | 5-HTP + DNK 333 (1 mg/kg po) | | |
| 1F | 4.4 | 28.6 | 22.4 | 650 | 21.7 |
| 2F | 10.7 | 24.4 | 15.4 | 228 | 36.9 |
| 3F | 4.5 | 19.8 | 11.4 | 440 | 42.4 |
| 4F | 4 | 15.1 | 10.5 | 378 | 30.5 |
| Mean | 5.9 | 22.0 | 14.9 | 423.8 | 32.9 |
| SEM | 1.6 | 2.9 | 2.7 | 87.5 | 4.5 |
| N | 4 | 4 | 4 | 4 | 4 |
| P RM ANOVA (post-hoc Turkey) | | | 0.045 vs 5-HTP | | |

| Micturition volume (g/17 hrs) | | | | 5-HTP % increase | DNK333 % inhibition |
|---|---|---|---|---|---|
| Animal | Control | 5-HTP (10 mg/kg sc) | 5-HTP + DNK 333 (3 mg/kg po) | | |
| 1G | 5.1 | 26.4 | 16.2 | 518 | 38.6 |
| 2G | 4.9 | 35 | 17.9 | 714 | 48.9 |
| 3G | 4.1 | 19.2 | 11.6 | 468 | 39.6 |
| 4G | 7.6 | 17.6 | 14.2 | 232 | 19.3 |
| Mean | 5.4 | 24.6 | 15.0 | 483.0 | 36.6 |
| SEM | 0.8 | 4.0 | 1.4 | 99.2 | 6.2 |
| N | 4 | 4 | 4 | 4 | 4 |
| P RM ANOVA (post-hoc Turkey) | | | 0.006 vs 5-HTP | | |
| Mean | 5.7 | 23.3 | | 453.4 | |
| SEM | 0.8 | 2.3 | | 62.2 | |
| N | 8 | 8 | | 8 | |
| P RM ANOVA (post-hoc Turkey) | | 0.001 vs Control | | | |

Example 2

Detrusor contractility is tested in longitudinal muscle-nerve preparations from the guinea-pig urinary bladder (Mackenzie and Burnstock 1984). In organ bath studies, isometric contractile responses are evoked by cumulative application of substance P (0.1 nM up to 30 μM). Substance P stimulates contractions in a concentration-dependent fashion ($pD_2$=6.68±0.23; mean±SEM; n=5 preparations). The compound of formula II (10 nM, 100 nM and 1000 nM) competitively inhibits substance P-evoked contractile responses; a Schild plot analysis (see FIG. 2) reveals a $pA_2$ value of 7.97 (slope: −0.98).

REFERENCES

Belis J A, Curley R M, Lang C M (1996) Bladder dysfunction in the spontaneously diabetic male Abyssinian-Hartley guinea pig. Pharmacology; 53(1):66-70.

Mackenzie I, Burnstock G (1984) Neuropeptide action on the guinea-pig bladder; a comparison with the effects of field stimulation and ATP. Eur J Pharmacol; 105(1-2):85-94.

The invention claimed is:

1. A method of treating urinary incontinence in a subject in need of such treatment that comprises administering to said subject an effective amount of a compound of formula II

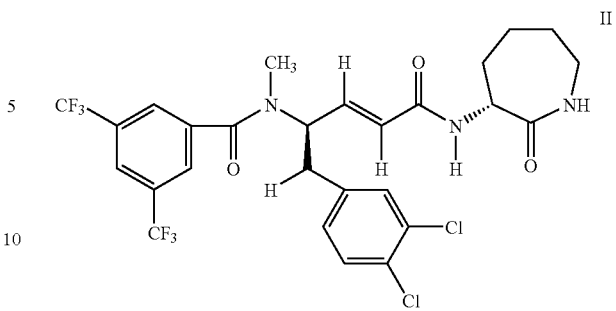

in free form or in the form of a pharmaceutically acceptable salt.

2. A method according to claim 1, in which the urinary incontinence is urge incontinence, stress incontinence, mixed urge/stress incontinence or neurogenic incontinence.

* * * * *